United States Patent [19]

Guerriero

[11] Patent Number: 4,570,621

[45] Date of Patent: Feb. 18, 1986

[54] CIRCULO-SEGMENTAL SPANNING AND HOLDING APPARATUS

[76] Inventor: Frederico D. Guerriero, 7029 West Grand, Chicago, Ill. 60635

[21] Appl. No.: 669,010

[22] Filed: Nov. 7, 1984

Related U.S. Application Data

[63] Continuation-in-part of Ser. No. 380,111, May 20, 1982, Pat. No. 4,409,971.

[51] Int. Cl.[4] .................................... A61F 5/04

[52] U.S. Cl. .................................... 128/84 C

[58] Field of Search .................... 128/84 C, 84 R, 75, 128/85, DIG. 20

[56] References Cited

U.S. PATENT DOCUMENTS 3,868,952 3/1975 Hatton ........................ 128/DIG. 20

4,409,971 10/1983 Guerriero ........................ 128/84 C

*Primary Examiner*—John D. Yasko

*Attorney, Agent, or Firm*—Robert M. Ward

[57] ABSTRACT

The present invention is directed to an orthopedic traction device which, in preferred embodiments, may be in the form of I-beam shaped elements or tubular elements, and such elements forming or operating in conjunction with an associated plurality of pressure plates for disposition intermittently disposed in spaced array about a selected anatomical portion for effecting traction. The pressure plates are spanned by at least one pressure strap such that intervening areas of the anatomical portion are not placed under pressure to retain circulation downstream thereof. A pivotably adjustable traction securement means is attached to the pressure plate on either side of the anatomical portion to permit adjustment of the angle of traction, thereby to vary the longitudinal distribution of the inwardly directed pressure on the pressure plates for adjusting the direction of the traction.

17 Claims, 14 Drawing Figures

FIG. 3
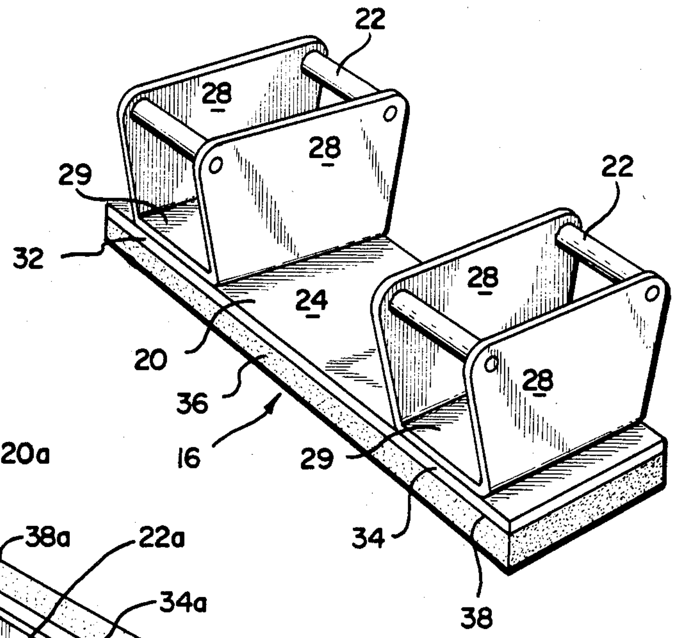
FIG. 4
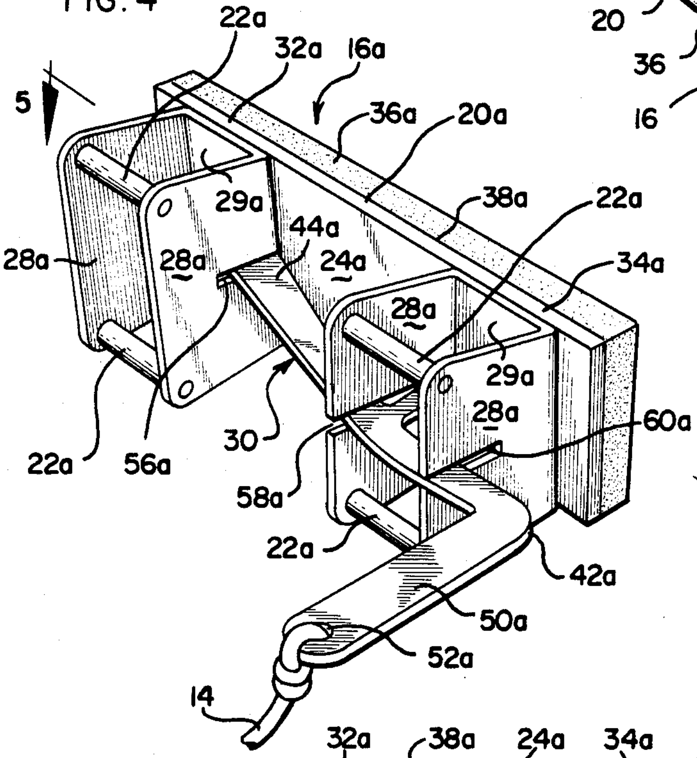
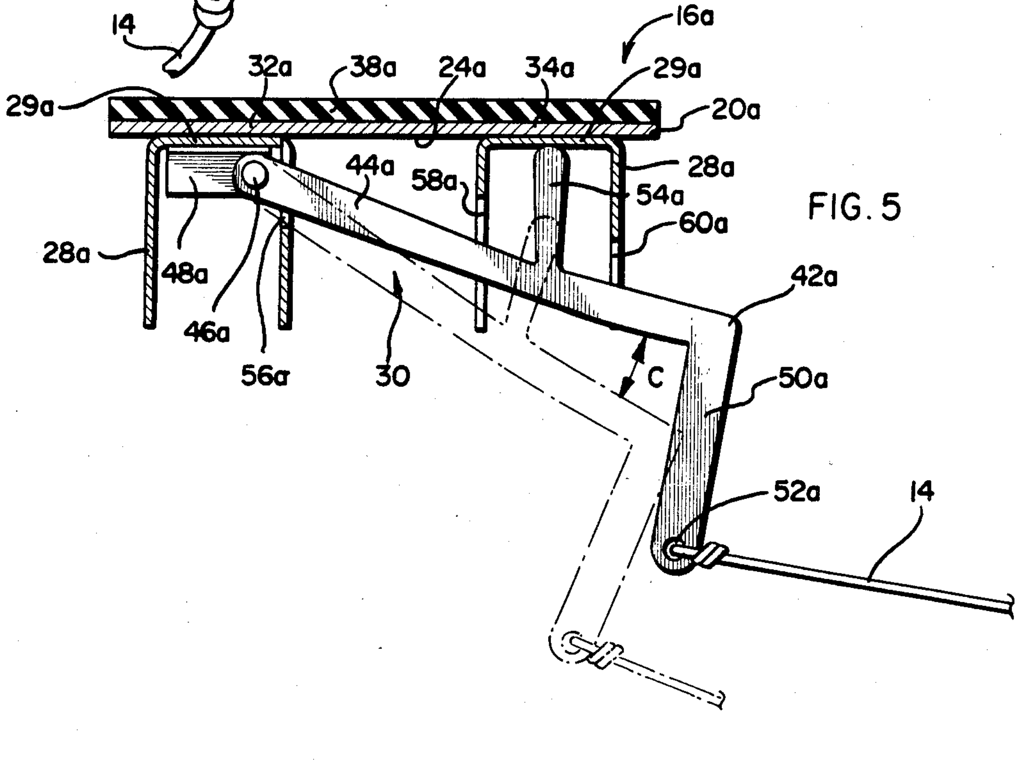
FIG. 5

CIRCULO-SEGMENTAL SPANNING AND HOLDING APPARATUS

BACKGROUND OF THE INVENTION

This application is a continuation-in-part of application Ser. No. 380,111 filed on May 20, 1982, now U.S. Pat. No. 4,409,971.

The present invention is directed generally to orthopedic devices, and more particularly to a circulo-segmental spanning and holding apparatus having means for adjusting the direction of the traction and means for adjusting the inwardly directed pressure of the apparatus against an anatomical portion.

In the prior art, certain anchorage means have been provided for the application of traction to an anatomical portion. In many instances, the prior art anchorage devices required the application of paste, tape or other adhesive substance against the skin with a circular bandage being applied around the anatomical portion. Such prior art structures have resulted in transmitting the force of the traction to the skin and to lower layers causing damage thereto.

In particular, such prior art devices have had inter alia the severe defect of effecting a sliding mechanism to lower anatomical layers including the application of longitudinally directed shear to the skin, which has had the further disadvantage of dispersing the force of traction to the anatomical layers, rather than to the skeletal structure requiring the traction. Additional disadvantges have been the causation of pain because of the shearing effect on the skin and because of the additional force necessary to effect the proper traction.

Also, many prior art devices which are secured by such adhesives have not been useable for any but limited time periods because of the degradation of the adhesive caused by constant shear and occasional movement of the patient. In many such instances, even slight movements of the patient, for example, in adjusting position to prevent loss of circulation and bed sores or muscle cramps, have risked the danger of causing the adhesively secured traction devices to disengage. Should disengagement occur, the possibility of further damage and discomfort to the patient is increased.

Yet additionally, the lack of reusability and the need of frequent replacement of adhesive-based systems has in such prior art systems increased unnecessarily the cost of supplying traction to the patient.

Accordingly, in view of the shortcomings and disadvantages of prior art devices, it is an object of the present invention to alleviate materially these conditions and to provide an improved orthopedic traction apparatus.

SUMMARY OF THE INVENTION

The orthopedic traction apparatus of the present invention comprises a plurality of intermittently disposed pressure plates which are disposed circulo-segmentally about an anatomical portion. The pressure plates include pressure strap spanning means elevated above the base portion thereof, such that a pressure strap, which is preferably adjustable as to its inwardly directed pressure, may be secured about the plates to provide an uniform pressure at equally distributed radial positions around the anatomical portion to which the traction apparatus of the present invention is applied.

A traction securement means which is pivotably adjustable is attached to preferably the distal end of the circulo-segmental plates for allowing a traction line to be angled, thereby to vary the longitudinal distribution of the inwardly directed pressure on the plates. Accordingly, greater or lesser pressure may be applied to the front or proximal portions of the plates, or to the rear or distal portions of the plates, as needed.

The novel structure of the circulo-segmental orthopedic traction apparatus of the present invention has resulted in an apparatus which is sturdy and reusable, thereby lowering the cost of the traction to the patient. Additionally, with the orthopedic traction apparatus of the present invention, a much greater force of traction may be applied with but minimal pain and discomfort to the patient. Moreover, the sliding of the traction apparatus along the skin resulting in a shearing action on the skin and lower layers with damaging consequences and pain to the patient associated with prior art devices has been minimized. Additionally, the circulo-segmental spanning feature of the orthopedic traction apparatus of the present invention allows for intervening radial areas to be free of any pressure, which permits for greater circulation to downstream anatomical areas.

An alternative preferred embodiment comprises a fibrous and polymeric net-like material which is moldable to the contours of the selected anatomical portion to form the circulo-segmental pressure plates. In such alternative preferred embodiment, the means for interconnecting the pressure plates and the spanning means comprises a plurality of cylindrical spanning tubes disposed in longitudinally mutually spaced array.

In a third alternative preferred embodiment, the circulo-segmental pressure plates are substantially in the form of an I-beam shape which is disposed to extend longitudinally along the anatomical portion requiring traction.

These and other advantages of the improved circulo-segmental spanning orthopedic traction apparatus of the present invention will become apparent to those skilled in the art in view of the following brief description of the drawings, detailed description of the preferred embodiments, appended claims, and accompanying drawings.

BRIEF DESCRIPTION OF THE DRAWINGS

FIG. 3 is a perspective view of one of the circulo-segmental plates as shown in FIGS. 1 and 2 of the kind for disposition above and below the leg, and comprising a resilient base portion disposed onto the underside of the base portion of the circulo-segmental pressure plate, and having upstandingly disposed from the upperside of the base portion respective interconnecting means for a plurality of roller-like pressure strap spanning means for receiving the pressure strap as shown in FIG. 2;

FIG. 4 is an accompanying circulo-segmental plate of the kind as shown in FIGS. 1 and 2 for abutting against the lateral and medial portions of the patient's leg and having pivotably adjustable traction securement means for allowing the traction line thereof to be adjustably angled, thereby to vary the longitudinal distribution of the inwardly directed pressure on the plates that is distributed to the patient's leg;

FIG. 5 is a longitudinal cross-sectional view taken along line 5—5 of FIG. 4 and showing in particular the L-shaped angle member with pivot securement means for limiting the range of pivotability of the L-shaped angle member inwardly and for bearing against the inner surface of the plate member to direct pressure thereagainst;

DETAILED DESCRIPTION OF THE PREFERRED EMBODIMENTS

Figure 1:
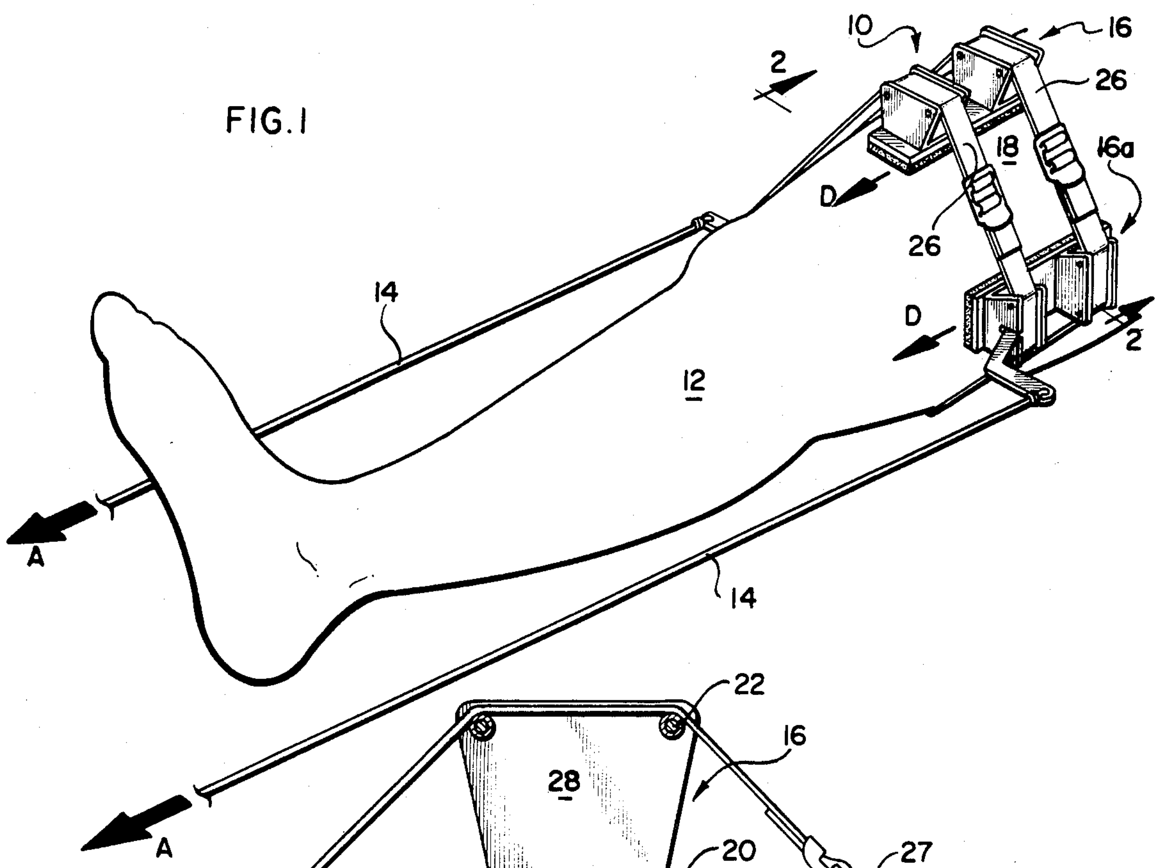
FIG. 1 is a perspective view showing the improved circulo-segmental orthopedic traction apparatus of the present invention applied to the leg of a patient undergoing traction in the direction as indicated by arrows A.

The orthopedic traction apparatus of the present invention is directed to various embodiments of devices for applying traction to a selected anatomical portion. The apparatus includes at least one, and preferably two, traction lines. A plurality of circulo-segmental plates are included for intermittent disposition in spaced radial array about the selected anatomical portion. The effect of such intermittent disposition is to retain circulation unimpeded in intervening areas between the pressure plates thereby to minimize circulatory problems downstream of the segmentally pressured anatomical portion against which the pressure plates of the orthopedic traction apparatus of the present invention are engaged. Each of the pressure plates comprises a base portion which is contoured to rest in substantially flat configuration against the anatomical portion. At least one pressure strap spanning means is disposed elevated from the base portion of the plate for pressure contact with the pressure strap means. Means are provided on and elevated above the upper surface of said pressure plate base portion for interconnecting the plate with the spanning means to retain the spanning means in spaced elevation from the said base portion.

At least one pressure strap is provided for disposition about the circulo-segmental plates. The pressure strap is affixed radially about the circulo-segmental plates and in firm contact with the strap spanning means for exerting an inward pressure thereon to hold the pressure plate sufficiently firmly against the anatomical portion. Thus, stable means for anchoring at least one traction line are disposed about and firmly secured to the anatomical portion.

Pivotably adjustable securement means are attached to at least one of the circulo-segmental plates for allowing the corresponding traction line to be adjustably angled. This adjustable angling feature of the circulo-segmental spanning traction apparatus of the present invention functions to vary the longitudinal distribution of the inwardly directed pressure on the pressure plates.

In preferred embodiments of the orthopedic traction apparatus of the present invention, the plates may preferably include a pair of pressure strap spanning means disposed substantially at each of the distal and proximal ends thereof. The pressure strap spanning means preferably includes at least one roller disposed longitudinally with respect to the base portion of the pressure plates, and thus longitudinally with respect to the selected anatomical portion, and transversely with respect to the pressure straps.

Other preferred embodiments of the orthopedic traction apparatus of the present invention may preferably include a pair of pressure straps urging both the proximal and distal ends of the base portion of the pressure plate inwardly and against the selected anatomical portion.

In preferred embodiments, the pressure plates also include a non-binding and resilient pad means secured to the inner surface of the base portion of the pressure plates. Such non-binding and resilient pad means serve to prevent longitudinally directed shearing action on the skin of the anatomical portion to which the pressure plates are applied, and also to prevent trauma to the inner layers of the anatomical portion caused by the inwardly directed pressure thereon.

In preferred embodiments, four of the pressure plates are spaced radially about the anatomical portion, for example, a leg—one each at the top, bottom, and each side of the anatomical portion.

The pivotably adjustable traction means in preferred embodiments may preferably comprise a generally L-shaped angle member. The L-shaped angle member in preferred embodiments has a generally longitudinally disposed first portion for pivotably connecting preferably to the upper surface of the distal end of the pressure plate. A generally transversely disposed second portion is connected to the longitudinally disposed first portion at one end thereof and is connected to the traction line at the opposite end thereof. Such L-shaped members preferably include a pivot stop means disposed opposite the second or traction line connecting portion thereof for bearing against the upper surface of the base portion of the pressure plate to limit the range of inward pivotability thereof.

Also in preferred embodiments, the pressure strap spanning interconnecting means includes aperture means for permitting inward motion of the proximal end of the first portion of the L-shaped angle member toward the upper surface of the base portion of the pressure plate.

The pressure strap utilized in the orthopedic traction apparatus of the present invention preferably includes adjustable means for varying the inwardly directed pressure on the circulo-segmental pressure plates.

In preferred embodiments, the pressure strap includes securement means for holding the pressure strap at a selected and stable tension in its radial disposition about the pressure plate. The pressure strap securement means may comprise in some embodiments hook and loop tape fastening means, such as is sold under the trademark "Velcro". In alternative preferred embodiments, a cinch buckle of the well-known variety may be utilized.

Whereas FIGS. 1–5 show one preferred embodiment of the circulo-segmental spanning and holding apparatus of the present invention, FIGS. 6–10 hereof show a second form of alternative preferred embodiment of the present invention. Such second alternative preferred embodiment includes as the circulo-segmental pressure plates at least two such plates, the base portion of which comprises a fibrous and polymeric net-like material which is moldable to the contours to the selected anatomical portion. Exelite, a registered trademark of the duPont Company of Wilmington, Del. is one suitable material for this purpose.

The means for interconnecting the pressure plates and the spanning means in this second preferred alternative embodiment comprises a plurality of cylindrical spanning tubes disposed in longitudinally mutually spaced array. The circulo-segmental pressure plates extend longitudinally for a substantial distance along the length of the selected anatomical portion. In such alternative preferred embodiments, the cylindrical spanning tubes correspondingly extend longitudinally also for a substantial distance along the length of the selected anatomical portion.

In such alternative preferred embodiments, at least one pressure strap comprising a plurality of turns of an elongated flat ribbon means is radially disposed about the cylindrical spanning tubes. Such elongated flat ribbon means thus functions to wrap and contain the other elements of the orthopedic traction apparatus of the present invention to exert inward pressure thereon for holding the cylindrical spanning tubes firmly against the fibrous and polymeric net-like plates.

Further, in such alternative preferred embodiments, the pivotably adjustable traction securement means preferably comprises clamp means which are secured at a site as selected along the fibrous and polymeric net-like plate for exerting the desired direction and magnitude of traction. The pressure straps utilized in such alternative preferred embodiments may preferably comprise a stretchable and elastic material such as may be used for compression bandages.

In these second embodiments, the cylindrical spanning tubes are disposed between an upper and lower layer of the fibrous and net-like material comprising the base portion of the circulo-segmental pressure plates. Preferably, in such embodiments, both the upper and lower layers of the fibrous and net-like material conform to the contours of the selected anatomical portion, except in areas where the upper layers dispose over one of the cylindrical spanning tubes. The cylindrical spanning tubes may be preferably formed from a plastic substance.

In a third preferred embodiment of the orthopedic traction apparatus of the present invention, each of the circulo-segmental pressure plates is substantially I-shaped in transverse cross-section to comprise an I-beam. The longitudinal dimension of the I-beam is disposed longitudinally along the anatomical portion requiring traction.

The base portion contoured to rest in substantially flat configuration against the anatomical portion comprises the base portion of the I-beam shaped pressure plate. In such third preferred embodiment, a pad is affixed to the underside of the base portion of the I-beam for protecting the anatomical portion requiring traction from irritation, bruising or trauma by the base portion. Such I-beam shaped pressure plates may preferably be comprised of aluminum or another metal, or in some instances, a plastic material.

The pressure strap spanning means in these latter preferred embodiments includes the top portion of the I-beam which is engaged by a preferably stretchable wrapping means as illustrated in the above second embodiment. The means interconnecting the plate and the spanning means comprises the central portion of the I-beam. The base and the top portion of the I-beam are connected to the ends of the central portion of the I-beam and are disposed perpendicularly thereto, and in generally parallel spaced array with respect to each other.

In such alternative third preferred embodiments of the present invention, the pivotably adjustable traction securement means comprises at least one aperture in the central portion of the I-beam near a longitudinal end thereof for holding the traction line therein. Preferably, an aperture is disposed near each longitudinal end of the central portion of the I-beam for adjustability and flexibility of use.

Referring now to the drawing in which common reference numerals are utilized for common elements, FIG. 1 shows a preferred embodiment of the circulo-segmental spanning traction apparatus of the present invention generally designated at 10 applied to leg 12 of a patient for effecting traction in the direction of arrows A.

Figure 2:
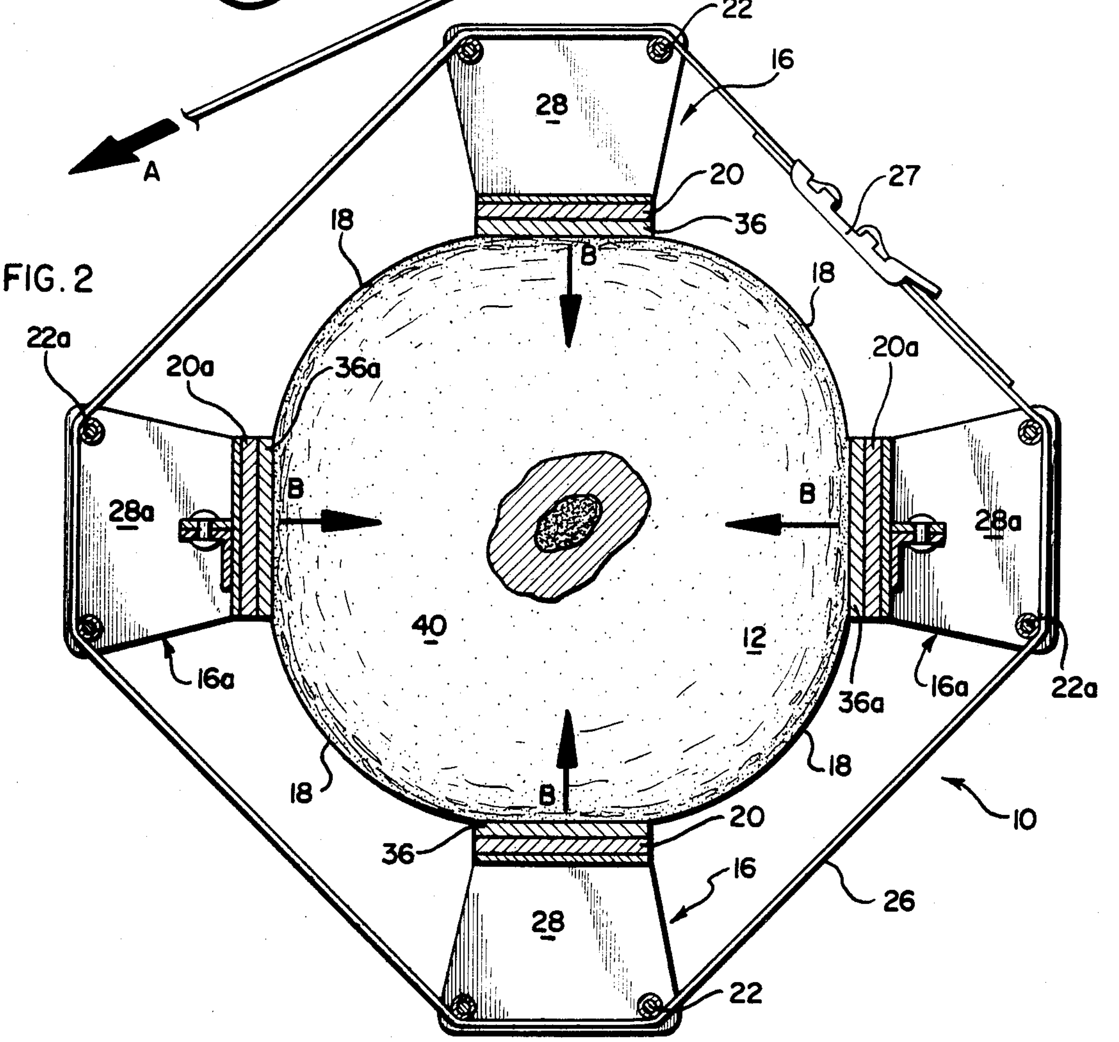
FIG. 2 is an enlarged transverse cross-sectional view taken along lines 2—2 of FIG. 1 showing the adjustable pressure strap disposed about the circulo-segmental pressure plates in contact with the pressure strap spanning means thereof to exert an inwardly directed pressure thereon to the patient's leg in the direction of arrows B, thereby to hold the pressure plates firmly against the leg and to provide stable means for anchoring the traction lines.

Orthopedic traction apparatus 10 includes preferably two traction lines 14, 14. A plurality of circulo-segmental plates of two different kinds generally 16 and **16*a* are included for intermittent disposition in spaced radial array about leg 12, as shown in FIGS. 1 and 2, although other anatomical portions may be selected for application thereto. In such disposition as shown in FIG. 1, the circulation is unimpeded in intervening areas 18 also shown in FIG. 2 between pressure plates 16, 16*a*, thereby to minimize circulatory problems downstream in leg 12. As is described hereinbelow in greater detail, there are two separate kinds of pressure plates 16, 16*a* utilized in orthopedic traction apparatus 10, and common elements utilize common reference numerals with the further designation _a to indicate the elements of the pressure plate 16*a*** having pivotably adjustable securement means associated therewith.

Each of the pressure plates **16, 16*a* comprises a base portion 20, 20*a* which is contoured to rest in substantially flat configuration against leg 12. Pressure strap spanning means shown in the form of rollers 22, 22*a* are disposed elevated from upper surface 24, 24*a* plate for pressure contact with pressure strap means 26. Pressure strap 26 includes a buckle 27 as shown in FIGS. 1 and 2, although other securement means may be utilized as described, supra. Upstanding wing plates 28, 28*a* serve as means on pressure plates 16, 16*a* for interconnecting the plate with the spanning roller means 22, 22*a* to retain spanning roller means 22, 22*a* in spaced elevation from base portion 20, 20*a*. Upstanding wing plates 28, 28*a* may preferably be formed as a one-piece channel having a channel bottom portion 29, 29*a* as shown in FIGS. 3, 4 and 5**.

As shown in FIG. 1 in particular, two pressure straps 26, 26 are provided for disposition about circulo-segmental pressure plates **16, 16*a*. Pressure straps 26, 26 are affixed radially about circulo-segmental plates 16, 16*a* and in firm contact with strap spanning roller means 22, 22*a* for exerting an inward pressure thereon as shown at arrows B in FIG. 2 to hold pressure plates 16, 16*a* sufficiently firmly against leg 12. Thus, stable means for anchoring traction lines 14, 14 are disposed about leg 12**.

As shown most particularly in FIGS. 4 and 5, pivotably adjustable securement means generally **30*a* are attached to circulo-segmental plates 16*a* for allowing the corresponding traction line 14 to be adjustably angled and pivoted as shown at arrow C in FIG. 5. This adjustable angling feature of circulo-segmental spanning traction apparatus 10 functions to vary the longitudinal distribution of the inwardly directed pressure on plates 16*a***.

As shown in the figures hereof, plates **16, 16*a* include a pair of pressure strap spanning roller means 22, 22 and 22*a*, 22*a* disposed substantially at each of distal end 32, 32*a* and proximal end 34, 34*a* thereof. Rollers 22, 22*a* are disposed longitudinally with respect to base portion 24, 24*a* of pressure plates 16, 16*a* and thus longitudinally with respect to leg 12 and transversely with respect to pressure straps 26, 26**.

Pressure plates **16, 16*a* have a non-binding and resilient pad means 36, 36*a* secured to the inner surface 38, 38*a* of base portion 20, 20*a* of the pressure plates 16, 16*a*. Pad means 36, 36*a* serve to prevent longitudinally directed shearing action on the skin of leg 12, as should otherwise occur in the direction of arrow D of FIG. 1, and also to prevent trauma to the inner layers 40 of leg 12 as shown in FIG. 2** in particular.

Pressure plates **16, 16*a* are spaced radially about leg 12 at the top, bottom and each side of leg 12. As shown in FIGS. 4 and 5, pivotably adjustable traction means 30 preferably comprises a generally L-shaped angle member 42*a*. L-shaped angle member 42*a* includes generally longitudinally disposed first portion 44*a* which is pivotably connected at pin 46*a* to pivot attachment bracket 48*a* as shown in FIG. 5. Pivot bracket 48*a* is in turn fixedly connected to upper surface 24*a* of plate 16*a*. Generally transversely disposed second portion 50*a* is connected to longitudinally disposed first portion 44*a* at one end thereof and is connected to traction line 14 at the opposite end thereof at traction line aperture 52*a*. L-shaped member 42*a* preferably includes a pivot stop member 54*a* disposed opposite second connecting portion 50*a* for bearing against base portion 20*a* of pressure plate 16*a* to limit the range of inward pivotability thereof as shown in FIG. 5. Additionally, wing plates 28*a* include slits 56*a*, 58*a* and 60*a* for permitting pivotable inward motion as shown in arrow C of FIG. 5 of the proximal end of first portion 44*a* of L-shaped angle member 42*a* toward upper surface 24*a* of base portion 20*a* of pressure plate 16*a***.

The circulo-segmental pressure plates including the base portion, pressure strap spanning means in the form of preferred rollers, and means for interconnecting the base portion of the plate and the rollers, as well as the L-shaped angle member, are preferably formed from a light metal, such as aluminum, although plastics may be used in other preferred embodiments. The non-binding and resilient pad means secured to the inner surface of the pressure plate base portion may comprise any of a variety of rubbers or polymeric or co-polymeric substances, either with or without gaseous bubbles entrained therein, or other substances dispersed therein. The pressure strap is preferably formed of nylon, and the securement means thereof may be formed of metal, plastic, or hook and loop tape.

Referring now to FIGS. 6–10 hereof which show an alternative preferred embodiment of the orthopedic traction apparatus generally 100 of the present invention, such alternative preferred embodiment 100 includes as the circulo-segmental pressure plates at least two such plates: upper plate 102 and lower plate 104. The base portions 103, 105 of plates 102, 104 comprise a fibrous and polymeric net-like material generally 107 as shown in particular in FIG. 10. Therein, a plurality of longitudinally directed fibers 110 are disposed and fixed in spaced array by means of a similar plurality of laterally disposed fibers 112, each of which is coated with a stiffening substance to provide a moldable, but yet flexible, material. As shown in FIGS. 6–10, material 107 is moldable to the contours to the selected anatomical portion, for example, a leg 106 as shown in FIGS. 6–9. Exelite, a registered trademark of the duPont Company of Wilmington, Del. is a suitable material for this purpose.

Figure 6:
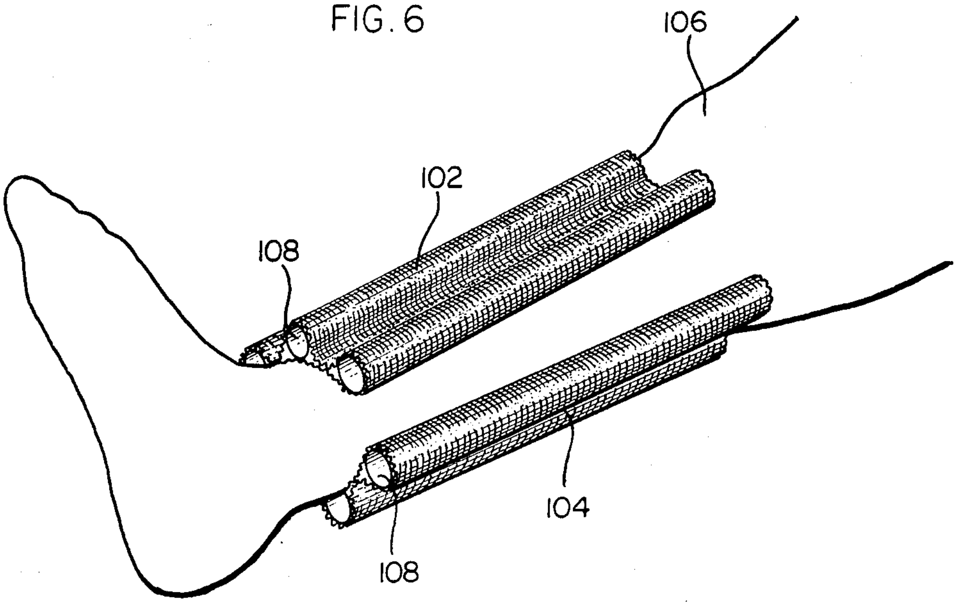
FIG. 6 is a perspective view of a second embodiment of the orthopedic traction apparatus of the present invention showing the fibrous and polymeric net-like material which is moldable to the contours of the patient's leg with means for interconnecting the pressure plate and the spanning means (not shown) in the form of a plurality of cylindrical spanning tubes disposed in longitudinally mutually spaced array on the patient's leg.
Figure 7:
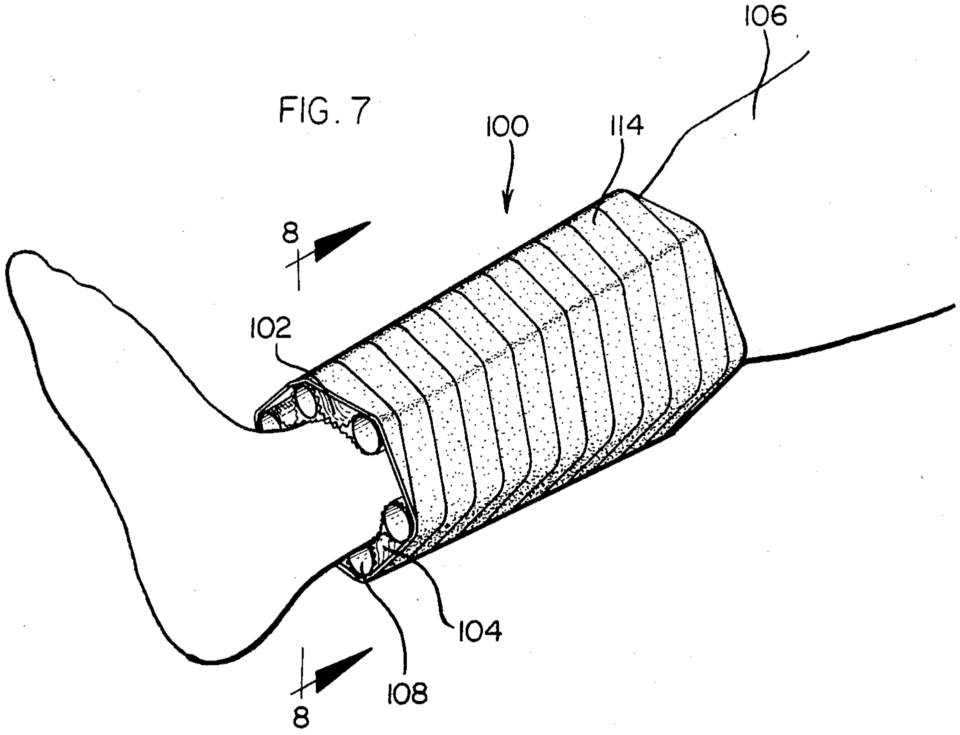
FIG. 7 is a perspective view of the alternative preferred embodiment as shown in FIG. 6, and further including the pressure strap in the form of a plurality of turns of an elongated flat ribbon material.

The means for interconnecting upper and lower pressure plates 102, 104 and the spanning means in the preferred alternative embodiment comprises a plurality of cylindrical spanning tubes 108 disposed in longitudinally mutually spaced array around leg 106. As shown in FIGS. 6 and 7, circulo-segmental pressure plates 102, 104 extend longitudinally for a substantial distance along the length of leg 106. In such alternative preferred embodiments, cylindrical spanning tubes 108 correspondingly extend longitudinally also for a substantial distance along the length of leg 106.

Figure 9:
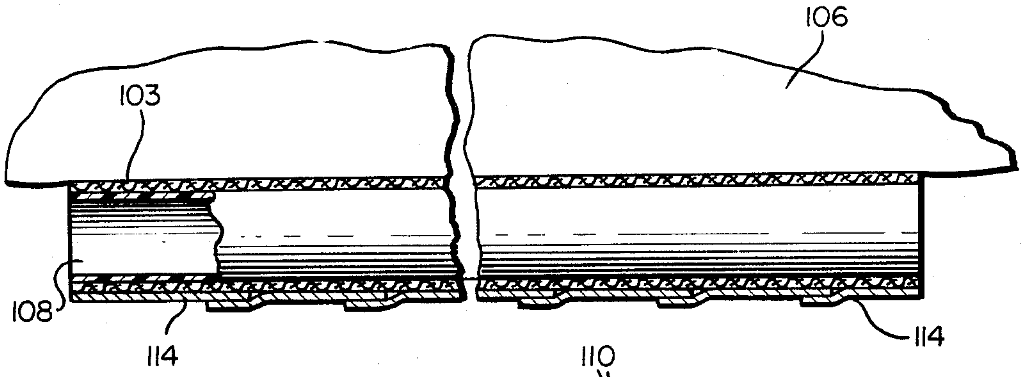
FIG. 9 is a greatly enlarged longitudinal cross-sectional view taken along line 9—9 of FIG. 8, and further showing disposed on the patient's leg the fibrous and net-like polymeric material surrounding the cylindrical spanning tube, all of which is wrapped to form the circulo-segmental spanning and holding apparatus with an elongated flat ribbon.
Figure 10:
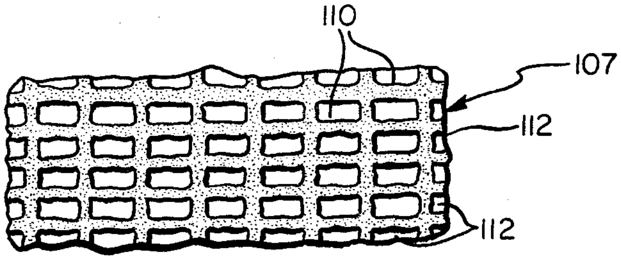
FIG. 10 is a greatly enlarged view of one form of the fibrous and polymeric net-like material which is suitable for use in forming the circulo-segmental pressure plates of the alternative preferred embodiment as shown in FIGS. 6–10 hereof.

In such alternative preferred embodiments, at least one pressure strap comprising a plurality of turns of an elongated flat ribbon 114 is radially disposed in overlapping disposition as shown more clearly in FIGS. 7 and 9, about cylindrical spanning tubes 108. Such elongated flat ribbon means 114 thus functions to wrap and contain the other elements of the orthopedic traction apparatus 100 of the present invention to exert inward pressure thereon for holding cylindrical spanning tubes 108 firmly against the fibrous and polymeric net-like plates 102, 104.

In such alternative preferred embodiments of FIGS. 6–10, the pivotably adjustable traction securement means preferably comprises clamp means of a design known to those having ordinary skill in the art, which clamps are secured at a site as selected along the fibrous and polymeric net-like plates 102, 104 for exerting the desired direction and magnitude of traction. The pressure straps 114 utilized may preferably comprise a stretchable elastic material.

Figure 8:
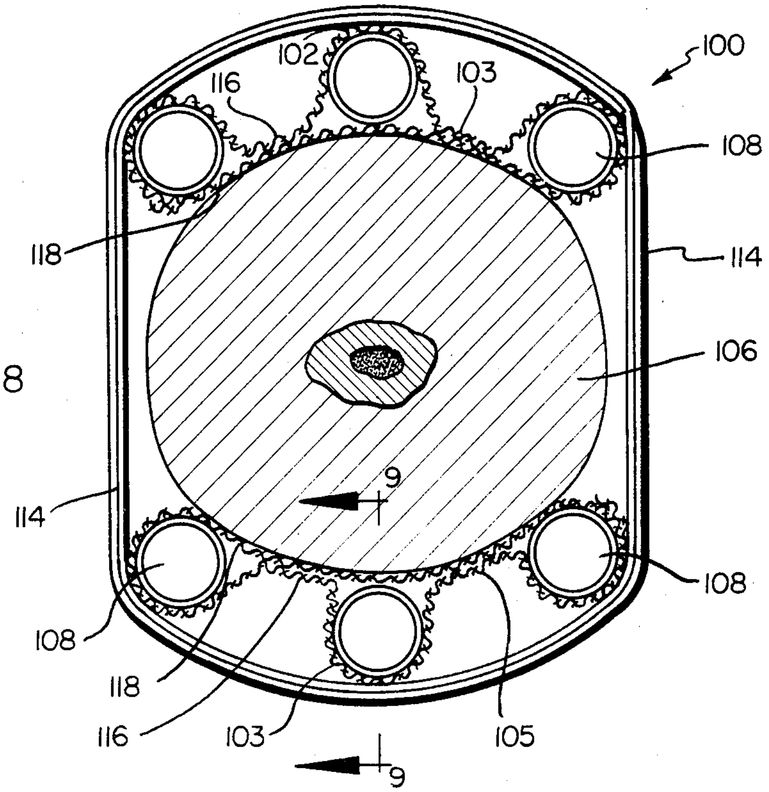
FIG. 8 is an enlarged transverse cross-sectional view taken along line 8—8 of FIG. 7, and showing disposed on the patient's lower leg, the fibrous and polymeric net-like material which has been molded to the contours of the leg on which is disposed the interconnecting means in the form of several cylindrical spanning tubes disposed in longitudinally mutually spaced array, and the elongated flat ribbon pressure strap radially disposed about the cylindrical spanning tubes for wrapping and containing thereof, as previously shown in FIG. 7.

In these embodiments, cylindrical spanning tubes 107 are preferably disposed between upper and lower layers 116, 118 as shown particularly in FIG. 8 of the fibrous and net-like material 107 comprising base portions 103, 105 of respective circulo-segmental pressure plates 102, 104. Preferably, in such embodiments, both upper and lower layers 116, 118 of fibrous and net-like material 107 conform of the contours of leg 106 except in areas where upper layer 116 is disposed over one of the cylindrical spanning tubes 108 as best shown in FIGS. 6 and 8.

Figures 11, 12, 13, 14:
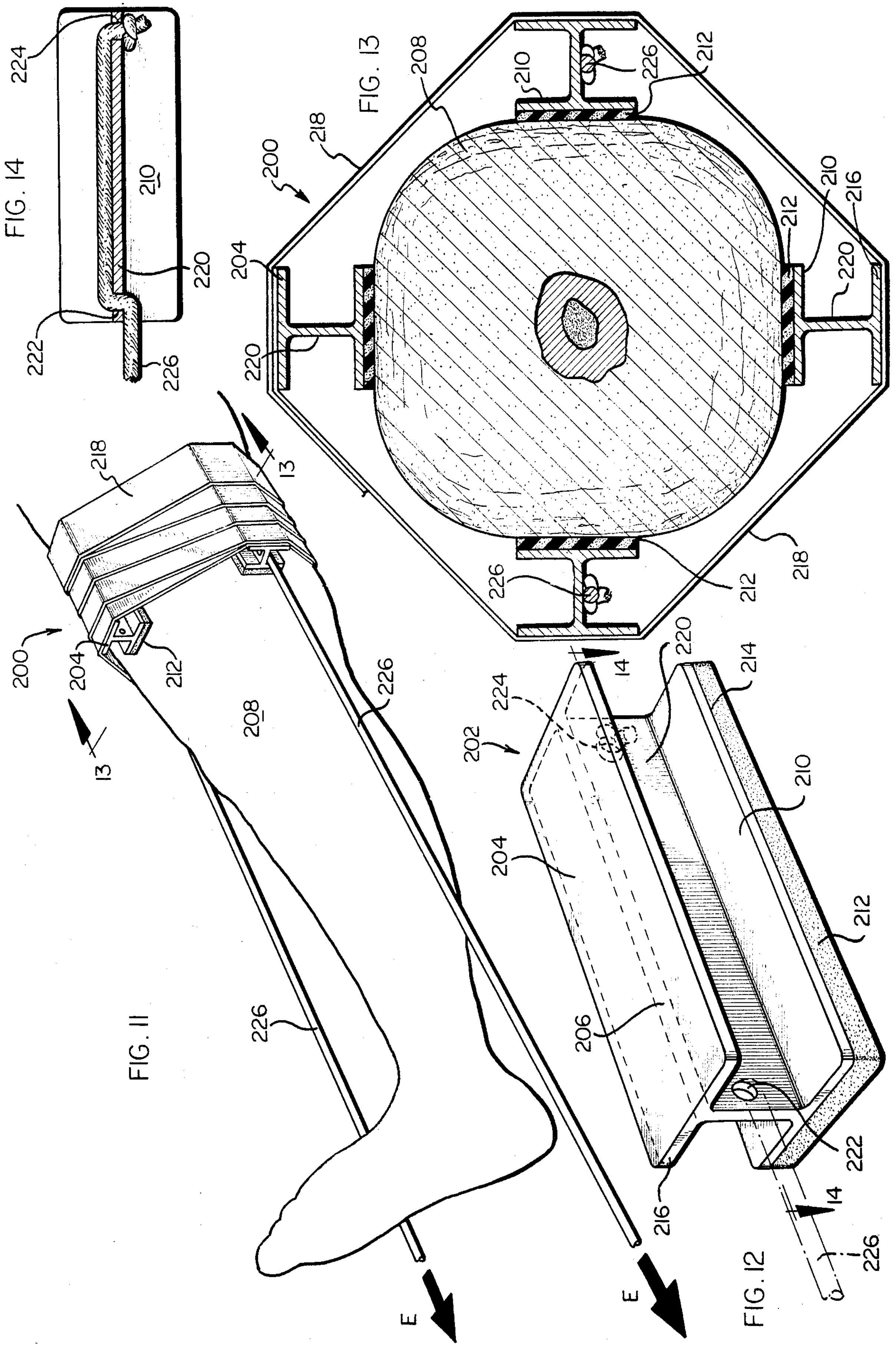
FIG. 11 is a perspective view of a third embodiment of the present invention showing circulo-segmental pressure plates in the form of I-beam shaped elements disposed about the patient's leg, and providing action thereto by means of associated traction lines extending longitudinally at the lateral and medial portions thereof.
FIG. 12 is a greatly enlarged perspective view of an I-beam shaped element as shown disposed in active configuration in FIG. 11, and showing traction line securing apertures on the middle portion thereof, and further showing padding means disposed on the lower portion thereof.
FIG. 13 is a somewhat enlarged lateral cross-sectional view taken along line 13—13 of FIG. 11 showing four (4) of said I-beam shaped elements engaging the leg of the user and disposed in evenly spaced array thereabout, and further showing the circulo-segmental pressure being applied to said leg to provide holding means for said traction lines through exerting compressive inward pressure on said leg, but avoiding such pressure in intervening spaces for beneficial circulation in said leg.
FIG. 14 is a reduced longitudinal cross-sectional view taken along line 14—14 of FIG. 12 showing the engagement of said traction line in and held by the traction line apertures of the I-beam shaped elements of the present invention.

A third preferred embodiment of the orthopedic traction apparatus generally 200 of the present invention is shown in FIGS. 11–14. In such third preferred embodiment 200, each of the circulo-segmental pressure plates generally 202 as shown in FIG. 12 is substantially I-shaped in transverse cross-section to comprise an I-beam 204. The longitudinal dimension 206 as shown in FIG. 12 of I-beams 204 is disposed longitudinally along leg 208.

Base portion 210 of I-beam 204 is contoured to rest in substantially flat configuration against leg 208. In such third preferred embodiments as shown in FIGS. 11–14, a pad 212 is affixed to the underside 214 of base portion 210 of the I-beam for protecting the anatomical portion, such as leg 208, from irritation, bruising or trauma by base portion 210. Such I-beam shaped pressure plates 202 may preferably be comprised of aluminum or another metal, or in some instances, a plastic material.

The pressure strap spanning means comprises the top portion 216 of the I-beam 204 which engages a flat and preferably elastic wrapping 218 as shown in FIGS. 11 and 13 to comprise the spanning means. Alternatively, straps could be used in place of wrapping 218.

The means interconnecting the base 210 and the spanning means wrapping 218 comprises the central portion 220 of I-beam 204. The base 210 and the top portion 216 of I-beam 204 are connected to the ends of central portion 220 of I-beam 204 and are disposed perpendicularly thereto along longitudinal dimension 206 as shown in FIG. 12, and are disposed in generally parallel spaced array with respect to each other.

In such alternative third preferred embodiments 200 of the present invention, the pivotably adjustable traction securement means comprises at least one front aperture 222 and perferably a second rear aperture 224 in central portion 220 of the I-beam near the longitudinal ends thereof for holding the traction line 226 therein as shown in FIGS. 12 (in phantom lines) and 14. Preferably, traction line 226 is knotted at an end passed through rear aperture 224, extended along the side of central portion 220, and through front aperture 222, to extend forwardly for connection to a pulley or other weighted holding means as indicated by arrows E, E in FIG. 11.

Although the invention has been described in terms of a preferred construction of a circulo-segmental spanning traction apparatus, it will be apparent to those skilled in the art that many alterations and modifications may be made without departing from the invention. Accordingly, all such alterations and modifications are intended to be considered as within the spirit and scope of the invention as defined by the appended claims.

What is claimed is:

1. An orthopedic traction apparatus for application to a selected anatomical portion for applying traction, said apparatus comprising:

at least one traction line;

a plurality of circulo-segmental pressure plates intermittently disposed in spaced radial array about the selected anatomical portion whereby circulation is unimpeded in intervening areas between said plates, each said plate comprising a base portion comprising a fibrous material molded to conform to the contours of the selected anatomical portion and contoured to rest in substantially flat configuration against the anatomical portion, at least one pressure strap spanning means disposed elevated from said plate for inwardly directed pressure contact with a pressure strap, and means interconnecting said plate and said spanning means for retaining said spanning means in spaced elevation from said pressure plate means base portion;

at least one pressure strap for disposition radially about said circulo-segmental plates and in firm contact with said strap spanning means for exerting an inward pressure thereon for holding said plates sufficiently firmly against the anatomical portion to provide stable means for anchoring said at least one traction line; and pivotably adjustable traction securement means attached to at least one of said circulo-segmental plates for allowing said at least one traction line to be adjustably angled for varying the longitudinal distribution of the inwardly directed pressure on said plates.

2. The orthopedic traction apparatus of claim 1 wherein said circulo-segmental pressure plates comprises at least two, and said base portion of said plates comprises a polymeric net-like material.

3. The orthopedic traction apparatus of claim 1 wherein said means interconnecting said plate and said spanning means comprises a plurality of cylindrical spanning tubes disposed in longitudinally mutually spaced array.

4. The orthopedic traction apparatus of claim 3 wherein said circulo-segmental pressure plates extend longitudinally for a substantial distance along the length of the selected anatomical portion.

5. The orthopedic traction apparatus of claim 4 wherein said cylindrical spanning tubes correspondingly extend longitudinally for a substantial distance along the length of the selected anatomical portion.

6. The orthopedic traction apparatus of claim 3 wherein said pressure strap comprises a plurality of turns of an elongated flat ribbon means radially disposed about said cylindrical spanning tubes for wrapping and containing thereof to exert an inward pressure thereon for holding said cylindrical spanning tubes firmly against said fibrous plates.

7. The orthopedic traction apparatus of claim 1 wherein said pivotably adjustable traction securement means comprises clamp means secured at a situs selected along said fibrous plate for exerting the desired direction and magnitude of traction.

8. The orthopedic traction apparatus of claim 1 wherein said pressure straps comprise a stretchable material.

9. The orthopedic traction apparatus of claim 3 wherein said cylindrical spanning tubes are disposed between an upper and a lower layer of said fibrous material comprising said base portion of said circulo-segmental pressure plates.

10. The orthopedic traction apparatus of claim 9 wherein both of said upper and lower layers of said fibrous material conform to the contours of the selected anatomical portion except in areas wherein said upper layer is disposed over one of said cylindrical spanning tubes.

11. An orthopedic traction apparatus for application to a selected anatomical portion for applying traction, said apparatus comprising:

at least one traction line;

a plurality of circulo-segmental pressure plates intermittently disposed in spaced radial array about the selected anatomical portion whereby circulation is unimpeded in intervening areas between said plates, each said plate comprising a base portion contoured to rest in substantially flat configuration against the anatomical portion, at least one pressure strap spanning means disposed elevated from said plate for inwardly directed pressure contact with a pressure strap, and means interconnecting said plate and said spanning means for retaining said spanning means in spaced elevation from said pressure plate means base portion, said pressure plate being substantially I-shaped in transverse cross-section to comprise an I-beam, the longitudinal dimension of which is disposed longitudinally along the anatomical portion requiring traction;

at least one pressure strap for disposition radially about said circulo-segmental plates and in firm contact with said strap spanning means for exerting an inward pressure thereon for holding said plates sufficiently firmly against the anatomical portion to provide stable means for anchoring said at least one traction line; and pivotably adjustable traction securement means attached to at least one of said circulo-segmental plates for allowing said at least one traction line to be adjustably angled for varying the longitudinal distribution of the inwardly directed pressure on said plates.

12. The orthopedic traction apparatus of claim 11 wherein said base portion contoured to rest in substantially flat configuration against the anatomical portion comprises the base of said I-beam shaped pressure plate.

13. The orthopedic traction apparatus of claim 11, further comprising a pad affixed to the underside of said base portion for protecting the anatomical portion from irritation, bruising or trauma by said base.

14. The orthopedic traction apparatus of claim 11 wherein said pressure strap spanning means comprises the top portion of said I-beam.

15. The orthopedic traction apparatus of claim 11 wherein said means interconnecting said plate and said spanning means comprises the central portion of said I-beam to the ends of which said base and said top portion of said I-beam are perpendicularly connected in generally parallel spaced array.

16. The orthopedic traction apparatus of claim 11 wherein said pivotably adjustable traction securement means comprises at least one aperture in said central portion of said I-beam near a longitudinal end thereof for holding said traction line therein.

17. The orthopedic traction apparatus of claim 16 wherein an aperture is disposed near each longitudinal end of said central portion of said I-beam.

* * * * *